United States Patent [19]
Hosaka et al.

[11] Patent Number: 4,954,343
[45] Date of Patent: Sep. 4, 1990

[54] DERMAL PHARMACEUTICAL PREPARATIONS

[75] Inventors: Yoshifumi Hosaka; Saburo Otsuka; Takashi Kinoshita; Yusuke Ito, all of Osaka, Japan

[73] Assignee: Nitto Electric Industrial Co., Ltd., Osaka, Japan

[21] Appl. No.: 406,200

[22] Filed: Sep. 12, 1989

Related U.S. Application Data

[63] Continuation of Ser. No. 175,985, Mar. 31, 1988, abandoned.

[51] Int. Cl.$^5$ .............................................. A61F 13/02
[52] U.S. Cl. ..................................... 424/448; 424/449
[58] Field of Search ................................ 424/448, 449

[56] References Cited

U.S. PATENT DOCUMENTS 4,752,478 6/1988 Bondi et al. .......................... 424/448

Primary Examiner—Ellis P. Robinson
Assistant Examiner—Leon R. Horne
Attorney, Agent, or Firm—Sughrue, Mion, Zinn, Macpeak & Seas

[57] ABSTRACT

A dermal pharmaceutical preparation comprising a soft support having provided thereon a pressure-sensitive adhesive layer containing a pressure-sensitive adhesive and a drug, wherein said pressure-sensitive adhesive is a copolymer comprising a (meth)acrylamide having an amino group as a comonomer unit. The preparation remains the drug in a dissolved state and is excellent in drug liberation and adhesion to the skin.

7 Claims, No Drawings

DERMAL PHARMACEUTICAL PREPARATIONS

This is a continuation of application Ser. No. 07/175,985, filed Mar. 31, 1988 now abandoned.

FIELD OF THE INVENTION

This invention relates to a dermal pharmaceutical preparation which is applied to the skin to percutaneously administer a drug.

BACKGROUND OF THE INVENTION

Conventional pharmaceutical preparations for percutaneous administration of a drug for the treatment or prevention of topical or systemic diseases include adhesive-backed tapes or sheetings comprising a support having provided thereon an adhesive layer containing an active ingredient such as methyl salicylate, menthol, etc.

In these dermal preparations, acrylic pressure-sensitive adhesives have been employed from the standpoint of adhesion to the skin, internal cohesiveness, and stability of the drug to decomposition with time.

Considering diffusion and delivery of a drug to the skin in percutaneous administration, it is desirable that the drug should be in a dissolved state in the pressure-sensitive adhesive. However, since many of the acrylic pressure-sensitive adhesives generally have poor hydrophilic properties, when a hydrophilic drug is incorporated into such an adhesive in an amount enough to produce significant pharmacological effects, the drug is liable to crystallize in the adhesive layer to cause problems of adhesion, diffusion, and liberation of the drug into the body.

SUMMARY OF THE INVENTION

As a result of extensive investigations, the present inventors have found that a pressure-sensitive adhesive comprising a copolymer of a (meth)acrylamide having an amino group in the molecule thereof exhibits excellent adhesion to the skin and also has a markedly increased polarity thereby to allow a large amount of a drug to exist in a dissolved state. It has also been found that the above-described (meth)acrylamide copolymer, when used as adhesive for percutaneous administration of the drug, ensures liberation and percutaneous permeation of the drug. The present invention has been completed based on these findings.

That is, the present invention relates to a dermal pharmaceutical preparation comprising a soft support having provided thereon a drug-containing pressure-sensitive adhesive layer, wherein said pressure-sensitive adhesive is a copolymer comprising a (meth)acrylamide having an amino group as a comonomer unit.

DETAILED DESCRIPTION OF THE INVENTION

The support which can be used in the present invention functions to retain a layer of a pressure-sensitive adhesive containing a drug and is selected from materials having moderate softness so as to follow the movement of the skin when applied thereto and not to cause uncomfortableness when applied to the part subject to bending.

Examples of the support meeting these requirements include films or sheets of plastics, e.g., polyolefins (e.g., polyethylene), polyester, polyvinyl chloride, polyvinylidene chloride, polyamide, ethylene-vinyl acetate copolymers, polyurethane, etc., rubber and/or synthetic resin foamed sheets or films, nonwoven cloth, woven cloth, paper, metal foils, and various laminates of these materials.

The thickness of the support is not particularly limited and is appropriately determined according to the material of the support. However, the thickness of the support is generally 2 to 2,000 $\mu$m and preferably 5 to 500 $\mu$m. If the thickness thereof is too small, it is difficult to obtain a sufficient strength and also it is difficult to handle the same due to the lack of self-supporting property. On the other hand, if the thickness thereof is too large, there is uncomfortable feeling when the pharmaceutical preparation is adhered on a skin.

The pressure-sensitive adhesive into which a drug is incorporated should exhibit adhesiveness to the skin for a prolonged period of time. The pressure-sensitive adhesive to be used in the present invention is characterized by containing a (meth)acrylamide having an amino group as a comonomer unit.

From the viewpoint of adhesion to the skin, internal cohesiveness, stability of the drug to decomposition, and retention of the drug, the acrylic pressure-sensitive adhesive to be used preferably contains at least 50% by weight of an alkyl (meth)acrylate having from 4 to 12 carbon atoms in the alkyl moiety thereof as a main comonomer.

Other examples of the main comonomer are vinyl ether and the like, but alkyl (meth)acrylate is preferred.

Specific examples of the alkyl (meth)acrylate comonomer are methyl (meth)acrylate, ethyl (meth)acrylate, propyl (meth)acrylate, butyl (meth)acrylate, pentyl (meth)acrylate, hexyl (meth)acrylate, heptyl (meth)acrylate, octyl (meth)acrylate, nonyl (meth)acrylate, decyl (meth)acrylate, undecyl (meth)acrylate, dodecyl (meth)acrylate, 2-ethylhexyl (meth)acrylate, etc.

For the purpose of imparting cohesiveness to the copolymer comprising the above-described alkyl (meth)acrylate and (meth)acrylamide having an amino group, the copolymer may further comprise functional monomers, such as hydroxyethyl acrylate, hydroxypropyl acrylate, (meth)acrylamide, dimethylacrylamide, etc., or a vinyl monomer, such as acrylonitrile, vinyl acetate, vinyl propionate, vinyl pyrrolidone, vinyl caprolactam, etc. For the purpose of further improving capacity of dissolving a drug, the copolymer may furthermore comprise hydrophilic alkoxyalkyl (meth)acrylate comonomers, e.g., methoxyethyl (meth)acrylate, ethoxyethyl (meth)acrylate, butoxyethyl (meth)acrylate, etc.

The above-described monomers additionally added can be used in an amount of up to 40% by weight, preferably 5 to 25% by weight, based on the weight of the copolymer adhesive. The amount of the additional monomers exceeding 40% by weight tends to adversely affect the adhesiveness to a skin or the stability of a drug.

The (meth)acrylamide having an amino group which can be used in the present invention is represented by formula (I):

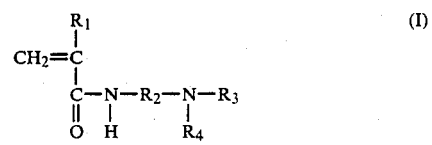

wherein $R_1$ represents a hydrogen atom or a methyl group; $R_2$ represents an alkylene group; and $R_3$ and $R_4$ each represents a hydrogen atom, an alkyl group, or a phenyl group.

The alkylene group in $R_2$ preferably has 1 to 8 carbon atoms. If the carbon atom number thereof is more than 8, the distance between amide group and amino group is too broad and the lowering of a polarity begins to occur, and as a result, there is the tendency that the solubility of a drug deteriorates. Further, the alkyl group in $R_3$ and $R_4$ preferably has 1 to 8 carbon atoms. If the carbon atom number thereof is more than 8, bulky side chains are formed, and when preparing a copolymer, the copolymerizability (reactivity) is lowered.

Taking solubility and releasability of a drug into consideration, preferred of the (meth)acrylamides of formula (I) are dialkylaminoalkyl (meth)acrylamides wherein the total number of carbon atoms in $R_2$, $R_3$, and $R_4$ is between 3 and 15.

Specific examples of the (meth)acrylamide of formula (I) include N,N-dimethylaminoethyl (meth)acrylamide, N,N-dimethylaminoethyl (meth)acrylamides, N,N-dimethylaminopropyl (meth)acrylamide, N,N-diethylaminopropyl (meth)acrylamide, N,N-dipropylaminopropyl (meth)acrylamide, N,N-di-n-butylaminoethyl (meth)acrylamide, etc.

The pressure-sensitive adhesive which can be used in the present invention is obtained by copolymerizing at least one of these (meth)acrylamides with at least one of the above-described polymerizable comonomers, and preferably alkyl (meth)acrylate monomers.

The (meth)acrylamide according to the present invention shows basicity attributed to the amido group and the amino group contained therein and, when used as comonomer, is believed to produce a pressure-sensitive adhesive having markedly increased polarity, exhibiting satisfactory dissolving power for drugs.

The copolymer adhesive preferably contains from 5 to 40%, and more preferably from 10 to 30%, by weight of the (meth)acrylamide of formula (I). If the (meth)acrylamide content is less than 5% by weight, the polarity of the resulting copolymer cannot be sufficiently increased. If so, a drug having high polarity would not be dissolved to a sufficient degree, readily resulting in crystallization in the adhesive layer, which becomes a bar to liberation or delivery of the drug. On the other hand, if the (meth)acrylamide content exceeds 40%, by weight, the cohesive force tends to become too high to assure adhesiveness to the skin.

The drug which can be used in the dermal preparations of the present invention is not particularly limited as far as it can permeate through the skin into the body when applied onto the skin.

Specific examples of the drug are corticosteroids, e.g., Hydrocortisone, Prednisolone, Beclomethasone dipropionate, Flumethasone, Triamcinolone, Triamcinolone acetonide, Fluocinolone, Fluocinolone acetonide, Fluocinolone acetonide acetate, Clobetasol propionate, etc.; anti-inflammatory analgestics, e.g., Acetaminophen, Mefenamic acid, Indomethacin, Diclofenac, Diclofenac sodium, Alclofenac, Oxyphen-butazone, Phenylbutazone, Ibuprofen, Flurbiprofen, salicylic acid, methyl salicylate, (menthol, camphor, Sulindac, Tolmethine sodium, Naproxen, Fenbufen, etc.; hypnotic analgesics, e.g., Phenobarbital, Amobarbital, Cyclobarbital, Lorazepam, Haloperidol, etc.; tranquilizers, e.g., Fluphenazine, Thioridazine, Diazepam, Flunitrazepam, Chloropromazine, etc.; antihypertensive agents, e.g., Clonidine, Clonidine hydrochloride, Pindolol, Propranolol, Propranolol hydrochloride, Bupranolol, Indenolol, Bucumolol, Nifedipine, Diltiazem hydrochloride, etc.; hypotensive diuretics, e.g., Hydrothiazide, Bendroflumethiazide, Cyclopenthiazide, etc.; antibiotics, e.g., Penicillin, Tetracyclin, Oxytetracylin, Neomycin, Erythromycin, Chloramphenicol, etc.; anesthetics, e.g. Lidocaine, Benzocaine, Ethyl aminobenzoate, etc.; antimicrobials, e.g., Benzalkonium chloride, Nitrofurazone, Nystatin, Acetosulfamine, Clotrimazole, etc.; antifungals, e.g., Pentamycin, Amphotericin B, Pyrrolnitrin, Clotrimazole, etc.; vitamins, e.g., Vitamin A, Ergocalciferol, Cholecalciferol, Octotiamine, Riboflavin tetrabutylate, etc.; antiepileptics, e.g., Nitrazepam, Meprobamate, Clonazepam, etc.; coronary vasodilators, e.g., Nitroglycerin, Nitroglycenol, Isosorbide dinitrate, Erythritol tetranitrate, Pentaerythritol tetranitrate, Propatylnitrate, etc.; antihistaminics, e.g., Diphenhydramine hydrochloride, Chlorpheniramine, Diphenylimidazole, etc.; antitussives, e.g., Dextromethorphan, Terbutaline, Ephedrine, Ephedrine hydrochloride, etc.; sex hormones, e.g., Progesterone, Estradiol, etc.; antidepressives, e.g., Doxepin; and others, e.g., 5-Fluorouracil, Dihydroergotamine, Fentanyl, Desmopressin, Digoxin, Metoclopramide, Donperidone, Scopolamine, Scopolamine hydrobromide, etc. These drugs may be used either individually or in combinations of two or more thereof.

The drug is added to the pressure-sensitive adhesive in an amount of from 0.1 to 30%, and preferably from 0.2 to 20%, by weight based on the total weight of the adhesive and the drug. Amounts of the drug less than 0.1% by weight would produce insufficient therapeutic effects, and the amounts exceeding 30% by weight not only pass the limit of possible therapeutic effects but prove bad economy.

Among the above-enumerated drugs, those having an acid-base structure and thereby highly hydrophilic properties are preferred because they are easily dissolved in the acrylic pressure-sensitive adhesive of the present invention and are excellent in diffusion and transfer to the skin. Hydrophilic drugs having an acid-base structure have at least one acidic group (e.g., a carboxyl group) and at least one basic group (e.g., an amino group) and often exhibit high polarity. The conventional acrylic adhesives which have been generally employed as pressure-sensitive adhesive from the standpoint of adhesion to the skin and the like are, in most cases, incapable of dissolving such hydrophilic drugs due to too low polarity.

To the contrary, since the acrylic pressure-sensitive adhesive used in the dermal pharmaceutical preparations according to the present invention contains a (meth)acrylamide having an amino group as comonomer unit, it possesses increased polarity as a whole due to the amido linkage. Therefore, even the hydrophilic drugs can be dissolved in the adhesive in high concentrations without undergoing crystallization.

The pressure-sensitive adhesive having dissolved therein a drug is coated on the above-described support by roll coating, cast coating, or the like coating technique to form a pressure-sensitive adhesive layer containing the drug. The thickness of the adhesive layer can be determined appropriately depending on the adhesiveness to the skin and the kind or dose level of the drug. The thickness thereof, however, is generally 5 to 1,000 μm, preferably 10 to 500 μm. If the thickness is too small, the adhesiveness to a skin is poor, and if the thickness is too large, an uncomfortable feeling occurs when adhering to the skin or it is disadvantageous from the standpoint of the amount of a drug effectively adsorbed (i.e., economical standpoint).

Thus, use of the (meth)acrylamide having an amino group as a comonomer markedly increases the total pressure-sensitive adhesive thereby greatly improving capability of dissolving a hydrophilic drug. Therefore, the preparations of the present invention are free from precipitation of the drug on the surface of the adhesive layer, i.e., blooming owing to the increased solubility of the drug in the adhesive, thus eliminating reduction of adhesiveness to the skin.

Further, since the hydrophilic properties of the pressure-sensitive adhesive can be increased due to the high polarity of the (meth)acrylamide having an amino group, the adhesive exhibits satisfactory adhesion and affinity for the skin, which improves releasability and percutaneous permeability of the drug. Moreover, the adhesive is compatible with a water content due to perspiration to enhance ODT (Occlusive Dressing Technique) effects.

The present invention is now illustrated in greater detail with reference to Examples and Comparative Examples, but it should be understood that the present invention is not limited thereto. In these examples, all the parts and percents are by weight unless otherwise indicated.

EXAMPLE 1

A monomer mixture consisting of 70 parts of 2-ethylhexyl acrylate, 20 parts of methyl methacrylate, and 10 parts of N,N-dimethylaminopropylacrylamide was stirred in a five-necked flask equipped with a stirring rod, a thermometer, a reflux condenser, an inlet for an inert gas, and a dropping funnel while displacing the atmosphere with an inert gas. To the mixture was added 0.2 part of azobisisobutyronitrile as polymerization initiator. The mixture was then allowed to react for 8 hours at a temperature controlled between 60° C. and 65° C. by selection of the stirring speed, cooling in an outer bath or dropwise addition of ethyl acetate as a diluent. The inner temperature was raised to 75° to 80° C., and the reaction mixture was aged at that temperature for 10 hours to obtain a pressure-sensitive adhesive solution having a solid content of 40%.

Clonidine, an antihypertensive, was added to the adhesive, solution, and the mixture was coated on a polyester film to a dry thickness of 40 $\mu$m, followed by drying to prepare a dermal pharmaceutical preparation containing 400 $\mu$g/cm$^2$ of Clonidine (Clonidine content: 10%).

EXAMPLE 2

A methanol solution of Scopolamine hydrobromide, an autonomic drug, was mixed with the same pressure-sensitive adhesive solution as prepared in Example 1, and the solution was coated on a polyester film to a dry thickness of 50 $\mu$m to prepare a dermal pharmaceutical preparation containing 1,000 $\mu$g/cm$^2$ of Scopolamine hydrobromide (Scopolamine hydrobromide content: 20%).

EXAMPLE 3

In a five-necked flask equipped with a stirring rod, a thermometer, a reflux condenser, an inlet for an inert gas, and a dropping funnel, 3 parts of polyoxyethylene lauryl ether was dispersed in 150 parts of water, and 70 parts of isononyl acrylate, 20 parts of methyl methacrylate, and 10 parts of N,N-dipropylaminobutylmethacrylamide were added to the dispersion. The mixture was heated up to 50° C. while displacing the atmosphere with an inert gas, and 0.1 part of potassium peroxodisulfate and 0.1 part of sodium sulfite were added thereto, followed by allowing the mixture to polymerize for 3 hours. The reaction mixture was aged at about 80° C. for 2 hours to prepare a pressure-sensitive adhesive emulsion having a solid content of 40%.

The resulting adhesive emulsion was subjected to salting out with a sodium sulfate aqueous solution, washed with water, and dried. The product was dissolved in ethyl acetate to obtain a pressure-sensitive adhesive solution having a solid content of 30%.

A methanol solution of Propranolol hydrochloride, an antihypertensive, was added to the adhesive solution, and the mixture was coated on a polyester film to a dry thickness of 40 $\mu$m to obtain a dermal pharmaceutical preparation containing 400 $\mu$g/cm$^2$ of Propranolol hydrochloride (Propranolol hydrochloride content 10%).

EXAMPLE 4

In a five-necked flask equipped with a stirring rod, a thermometer, a reflux condenser, an inlet for an inert gas, and a dropping funnel, a monomer mixture consisting of 60 parts of 2-ethylhexyl acrylate, 20 parts of t-butyl methacrylate, 10 parts of 2-methoxyethyl acrylate, and 10 parts of N,N-dimethylaminopropylacrylamide was stirred while thoroughly displacing the atmosphere with an inert gas. To the mixture was added 0.2 part of azobisisobutyronitrile as polymerization initiator, and the mixture was allowed to react for 8 hours at a temperature controlled between 60° C and 65° C. by selection of the stirring speed, cooling in an outer bath, or dropwise addition of ethyl acetate as a diluent. The reaction mixture was then heated up to 75° to 80° C., at which the mixture was aged for 10 hours to obtain a pressure-sensitive adhesive solution having a solid content of 40%.

A methanol solution of Clonidine hydrochloride, an antihypertensive, was mixed with the adhesive solution, and the mixture was coated on a polyester film to a dry thickness of 40 $\mu$m and dried to obtain a dermal pharmaceutical preparation containing 600 $\mu$g/cm$^2$ of Clonidine hydrochloride (Clonidine hydrochloride content 15%).

COMPARATIVE EXAMPLE 1

A pressure-sensitive adhesive solution (solid content: 40%) was prepared in the same manner as in Example 1, except for excluding N,N-dimethylaminopropylacrylamide from the monomer mixture Clonidine, an antihypertensive, was added to the adhesive solution, and the mixture was coated on a polyester film to a dry thickness of 40 $\mu$m, followed by drying to obtain a dermal pharmaceutical preparation having a Clonidine content of 400 $\mu$g/cm$^2$ (10%).

COMPARATIVE EXAMPLE 2

A monomer mixture consisting of 90 parts of 2-ethylhexyl acrylate and 10 parts of acrylic acid was stirred in a five-necked flask equipped with a stirring rod, a thermometer, a reflux condenser, an inlet for an inert gas, and a dropping funnel while thoroughly displacing the atmosphere with an inert gas. To the mixture was added 0.2 part of benzoyl peroxide as polymerization initiator, and the mixture was allowed to react for 8 hours at a temperature controlled between 60° C. and 65° C. by selection of the stirring speed, cooling in an outer bath or dropwise addition of ethyl acetate as a diluent. The inner temperature of the reaction mixture was raised up to 75° to 80° C., and the mixture was aged at that temperature for 10 hours to obtain a pressure-sensitive adhesive solution having a solid content of 30%.

A methanol solution of Scopolamine hydrobromide, an autonomic drug, was mixed with the resulting adhesive solution, and the mixture was coated on a polyester film to a dry thickness of 50 μm and dried to prepare a dermal pharmaceutical preparation containing 1,000 μg/cm$^2$ (20%) of Scopolamine hydrobromide.

COMPARATIVE EXAMPLE 3

A pressure-sensitive adhesive solution (solid content: 30%) was prepared in the same manner as in Example 3, except for excluding N,N-dimethylaminopropylacrylamide from the monomer mixture. A methanol solution of Propranolol hydrochloride, an antihypertensive, was mixed with the adhesive solution, and the resulting mixture was coated on a polyester film to a dry thickness of 40 μm and dried to obtain a dermal pharmaceutical preparation having a Propranolol hydrochloride content of 400 μg/cm$^2$ (10%).

COMPARATIVE EXAMPLE 4

A pressure-sensitive adhesive solution (solid content: 40%) was prepared in the same manner as in Example 4, except for excluding N,N-dipropylaminobutylacrylamide from the monomer mixture. A methanol solution of Clonidine hydrochloride, an antihypertensive, was mixed with the adhesive solution, and the resulting mixture was coated on a polyester film to a dry thickness of 40 μm to prepare a dermal pharmaceutical preparation containing 600 μg/cm$^2$ (15%) of Clonidine hydrochloride.

Each of the preparations obtained in the foregoing Examples and Comparative Examples was cut to a circle of 3 cm in diameter and tested according to the following test methods to evaluate drug dissolving property, stability of the drug with time, drug releasability, adhesion to the skin, and irritation to the skin. The results obtained are shown in Table 1 below.

(1) Drug Dissolving Property

The same piece was allowed to stand at 25° C. for 24 hours, and the state of the drug in the preparation was observed and rated as follows.

Good . . The drug was in a dissolved state.
Bad . . Crystals of the drug were precipitated on the entire surface of the preparation.

(2) Stability of Drug with Time

The sample piece was sealed into an aluminum package and preserved at 25° C. or 50° C. for 1 month. The sample was then extracted with methanol, and the drug in the extract was quantitatively determined by high performance liquid chromatography to obtain a percent remainder.

(3) Drug Releasability

The sample piece was attached to the skin of a rat, and the total amount of the drug liberated through the skin into distilled water over a period of 24 hours was measured by high performance liquid chromatography. The result was relatively expressed taking that of the corresponding comparative example as a standard (1.0).

(4) Adhesion to the Skin

The sample piece was attached to the inside of a human upper arm, and the state of adhesion to the skin after 24 hours was visually observed and rated as follows.

Good . . 90% or more of the entire area still adhered.
Bad . . 50% or more and less than 90% of the entire surface still adhered.

(5) Irritation to the Skin

The sample piece was attached to the human back for 24 hours and then peeled off. One hour after the peeling, the state of the skin was visually observed and rated on the following basis.

0 . . No reaction occurred.
0.5 . . Slight red spots appeared.
1.0 . . Obvious red spots appeared.
2.0 . . Red spots and papules or edema appeared.
3.0 . . Red spots, edema, and papules or small blisters appeared.
4.0 . . Blisters appeared.

The results of the above rating for 10 panelists were averaged, and the average was rated on the following basis.

Average less than 1.0 . . minimal
Average of 1.0 or more . . moderate
Average of 2.0 or more . . severe

TABLE 1

|  | Example 1 | Example 2 | Example 3 | Example 4 | Comparative Example 1 | Comparative Example 2 | Comparative Example 3 | Comparative Example 4 |
|---|---|---|---|---|---|---|---|---|
| Drug Dissolving Property | good | good | good | good | good | bad | bad | bad |
| Stability of Drug: (%) | | | | | | | | |
| at 25° C. | 99.9 | 96.7 | 98.0 | 98.7 | 99.0 | 98.5 | 96.4 | 99.2 |
| at 50° C. | 99.9 | 92.3 | 96.3 | 98.5 | 98.7 | 97.2 | 95.7 | 99.0 |
| Relative Drug Releasability | 2.38 | 11.05 | 8.92 | 14.08 | 1.0 | 1.0 | 1.0 | 1.0 |
| Adhesion to the Skin | good | good | good | good | bad | bad | bad | bad |
| Non-Irritativeness | minimal | minimal | minimal | minimal | minimal | minimal | minimal | minimal |

It can be seen from Table 1 that the dermal pharmaceutical preparations according to the present invention are superior to the comparative preparations in capability of dissolving drugs, drug releasability, and adhesion to the skin. Also, they are by no means inferior to the comparative preparations in terms of stability of drugs and nonirritativeness to the skin.

As described above, the pressure-sensitive adhesive used in the dermal pharmaceutical preparations of the present invention have very high polarity and are thereby capable of dissolving hydrophilic drugs because the pressure-sensitive adhesive comprises an amino-containing (meth)acrylamide as a monomer unit. The high hydrophilic property of the adhesive brings about satisfactory adhesion and affinity to the skin and also ensures compatibility with water due to perspiration to thereby increase ODT effects, ultimately leading to excellent drug releasability and permeability through the skin.

While the invention has been described in detail and with reference to specific embodiments thereof, it will be apparent to one skilled in the art that various changes and modifications can be made therein without departing from the spirit and scope thereof.

What is claimed is:

1. A dermal pharmaceutical preparation comprising a soft support having provided thereon a pressure-sensitive adhesive layer containing a pressure-sensitive adhesive and a drug in the amount of 0.1 to 30% by weight based on the total weight of said adhesive and drug wherein said pressure-sensitive adhesive is a copolymer comprising a (meth)acrylamide having an amino group as a comonomer unit, wherein the (meth)acrylamide having an amino group is represented by formula (I):

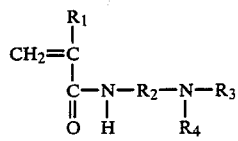

wherein $R_1$ represents a hydrogen atom or a methyl group; $R_2$ represents an alkylene group; and $R_3$ and $R_4$ each represents a hydrogen atom, an alkyl group, or a phenyl group.

2. A dermal pharmaceutical preparation as claimed in claim 1, wherein said (meth)acrylamide having an amino group is a dialkylaminoalkyl (meth)acrylamide having from 3 to 15 total carbon atoms in the alkyl moieties thereof.

3. A dermal pharmaceutical preparation as claimed in claim 1, wherein said copolymer contains from 5 to 40% by weight of the (meth)acrylamide having an amino group.

4. A dermal pharmaceutical preparation as claimed in claim 1, wherein said copolymer contains from 10 to 30% by weight of the (meth)acrylamide having an amino group.

5. A dermal pharmaceutical preparation as claimed in claim 1, wherein said copolymer further contains at least 50% by weight of an alkyl (meth)acrylate having from 4 to 12 carbon atoms in the alkyl moiety thereof.

6. A dermal pharmaceutical preparation as claimed in claim 1, wherein said drug is a hydrophilic drug.

7. A dermal pharmaceutical preparation as claimed in claim 1, wherein said drug is present in an amount of from 0.2 to 20% by weight based on the total weight of the pressure-sensitive adhesive and the drug.

* * * * *